United States Patent [19]

Gallagher et al.

[11] Patent Number: 5,097,004

[45] Date of Patent: Mar. 17, 1992

[54] NOVEL POLYESTERS AND THEIR USE IN COMPOSTABLE PRODUCTS SUCH AS DISPOSABLE DIAPERS

[75] Inventors: Francis G. Gallagher; Cathy J. Hamilton; Raymond F. Tietz, all of Wilmington, Del.

[73] Assignee: E. I. Don Pont de Nemours and Company, Wilmington, Del.

[21] Appl. No.: 645,849

[22] Filed: Jan. 25, 1991

Related U.S. Application Data

[63] Continuation-in-part of Ser. No. 522,134, May 11, 1990, Pat. No. 5,053,482.

[51] Int. Cl.$^5$ .............................................. C08G 63/20
[52] U.S. Cl. ................................... 528/272; 528/295; 528/301; 528/302; 528/308.6; 525/437; 525/450; 525/471; 428/480
[58] Field of Search ............... 528/272, 295, 301, 302, 528/308.6; 525/437, 450, 471; 428/480

[56] References Cited

U.S. PATENT DOCUMENTS

| | | | |
|---|---|---|---|
| 3,018,272 | 1/1962 | Griffing et al. | 528/293 |
| 3,853,820 | 12/1974 | Vachon | 528/295 |
| 4,217,441 | 3/1978 | Bayless | 528/293 |
| 4,418,116 | 11/1983 | Scott | 428/288 |
| 4,483,976 | 11/1984 | Yamamoto et al. | 528/275 |
| 4,526,738 | 7/1985 | Miyoshi et al. | 264/176 |
| 4,704,329 | 11/1987 | Hancock et al. | 428/369 |
| 4,883,706 | 11/1989 | Grosjean | 428/215 |

OTHER PUBLICATIONS

Ingamells, J. Appl. Poly. Sci., vol. 26, 4087-4101 (1981).
Grassie, Developments in Polymer Degradation-5, 112-119 (1984), Applied Science Publishers.

Primary Examiner—John Kight, III
Assistant Examiner—Sam A. Acquah

[57] ABSTRACT

The invention provides a novel polyesters, fibers and films, nonwovens from the fibers and disposable products of the polyesters such as diapers. The products are degradable under the conditions typically existing in waste composting processes, have low ingredient costs and yet provide strength and toughness properties adequate for end uses such as in disposable diapers. The polyesters are based upon polyethylene terephthalate copolymerized with a polyethylene glycol and a 5-sulfoisophthalic acid and, if desired, a polyethylene ether such as diethylene glycol.

12 Claims, No Drawings

NOVEL POLYESTERS AND THEIR USE IN COMPOSTABLE PRODUCTS SUCH AS DISPOSABLE DIAPERS

CROSS-REFERENCE TO RELATED APPLICATIONS

This Application is a continuation-in-part of copending parent application Ser. No. 07/522,134, filed by Tietz, May 11, 1990, U.S. Pat. No. 5,053,482.

FIELD OF THE INVENTION

This invention relates to novel polyesters and products therefrom. The products include fibers, films, nonwovens from the fibers and disposable products such as diapers from such products. The products are degradable to innocuous materials under conditions used in municipal solid waste composting systems.

BACKGROUND OF THE INVENTION

The inadequate treatment of municipal solid waste which is being put in landfills and the increasing addition of nondegradable materials, including plastics, to the municipal solid waste streams are combining to reduce drastically the number of landfills available and to increase the costs of municipal solid waste disposal. While the recycling of reusable components of the waste stream is desirable in many instances, there are some products which do not readily fit into this framework, e.g. disposable personal absorbents such as diapers and sanitary napkins, garbage bags, and numerous other products. The composting of non-recyclable solid waste is a recognized and growing method of reducing solid waste volume for landfilling and/or making a useful product from the waste to improve the fertility of fields and gardens. One of the limitations to marketing such compost is the visible contamination by undegraded plastic such as film and fiber fragments.

As related in the aforesaid parent application, Tietz was faced with several objectives, as follows:

1—to provide components which are useful in disposable products and which are degraded into less contaminating forms under the conditions typically existing in waste composting processes. These conditions may involve temperatures no higher than 70° C., and averaging more nearly 55° C.–60° C., humid conditions as high as 100% relative humidity, and exposure times which range from two weeks to more than three months.

2—to provide disposable components which will not only degrade aerobically in composting, but will continue to degrade in the soil or landfill anaerobically. As long as water is present, they will continue to break down into low molecular weight fragments which can be ultimately biodegraded by microorganisms completely into biogas, biomass and liquid leachate, as for natural organics like wood.

3—to provide novel polyesters for making the aforementioned fibers, films, coatings and nonwoven sheets of the polyesters, and disposable diapers containing the nonwoven sheets.

4—to provide polyesters and derivative products which have low ingredient costs and yet provide strength and toughness properties adequate for end uses such as in disposable diapers.

Accordingly, Tietz invented useful novel polyesters consisting essentially of recurring structural units of the formula

—C(O)—R—C(O)—OGO— wherein R is
about 97 to 99.9 mole % para-phenylene (abbreviation T) and
about 0.1 to 3 mole % of a sulfonate radical (abbreviation 5SI)

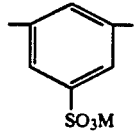

where M is an alkali metal or alkaline earth metal,
and wherein G is
about 60 to 80 mole % —$CH_2$—$CH_2$—(abbreviation 2G) and
about 20 to 40 mole % —$(CH_2)_2$—O—$(CH_2)_2$—(abbreviation DEG),
and especially wherein R is about 98 mole % para-phenylene (T) and about 2% of the sulfonate radical (5SI) and G is about 80 mole % —$CH_2$—$CH_2$— (2G) and about 20 mole % —$(CH_2)_2$—O—$(CH_2)_2$— (DEG), and fibers, non-woven sheet, films and combinations thereof, and disposable diapers comprising such materials. Such polyesters are useful for some end uses, e.g., as described by Tietz. For other end uses, however, it would be desirable to provide degradable materials having properties better adapted for such different end uses. In particular, it is desirable to provide polyesters that can be formed into films that have still further improved toughness, but with similar advantageous properties in many respects, as regards the polyesters that have been specifically disclosed by Tietz.

DESCRIPTION OF RELATED ART

Various polyester compositions have been suggested in the past for biodegradable end uses. These include polyhydroxybutyrate, polylactide, polycaprolactone, polyglycolide, and their copolymers. They have not been widely adopted in high volume uses, however, because they are either too expensive or their properties are inadequate for the uses mentioned above.

It is also known to use the salts of 5-sulfoisophthalic acid and its esters as comonomers to improve acid dyeability of polyethylene terephthalate fibers, see for example U.S. Pat. No. 3,018,272 (Griffing et al.). Moreover, this type of fiber is known to have an increased rate of hydrolytic degradation, see for example J. Appl Poly. Sci., vol. 26, 4087–4094 (W. Ingamells et al.) and Developments in Polymer Degradation 5, edited by N. Grassie, Applied Science Publishers, 1984, pages 112–119. The use of 5-sulfoisophthalate salts together with other neutral comonomers has been disclosed to increase dye rates, but the proportion of the neutral comonomer is usually minimized to affect physical properties as little as possible, see for example U.S. Pat. No. 4,704,329 (Hancock et al.) and U.S. Pat. No. 3,853,820 (Vachon).

It is also known to use as much as 20 to 45 mole % terephthalic to provide polyesters having suitable melting and bonding characteristics for a nonwoven binder fiber, see for example U.S. Pat. No. 4,418,116 (Scott).

Further, it is known to prepare water dispersible papermaking binder fibers which are made containing 5 to 20 mole % of diethylene glycol and preferably more than 3 mole % 5-sulfoisophthalate, see for example U.S. Pat. No. 4,483,976 (Yamamoto et al.).

In the latter patent each of the specific polymers disclosed contain 7 mole % or more of the 5-sulfoisophthalate salt.

SUMMARY OF THE INVENTION

The present invention is based on our finding that the polyesters of the parent Tietz application may be advantageously modified by including in the molecule, as part of the glycol (G) units, a small proportion of a lower alkylene polyalkylene glycol, such as polyethylene glycol (abbreviation PEG) of a specific molecular weight (abbreviation MW) that is relatively low, such as 600.

In one embodiment of the invention there is, accordingly, provided a novel fiber and film forming polyester consisting essentially of recurring structural units of the Formula (I)

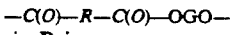

wherein R is
about 97 to 99.9 mole % para-phenylene (T) and
about 0.1 to 3 mole % of 5SI sulfonate radical

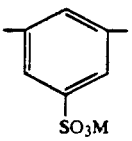

where M is
an alkali metal or alkaline earth metal, and wherein G is at least about 13% by weight of a radical of a polyalkylene glycol of (number average) molecular weight (MW) at least about 250, up to about 40 mole % of a polyethylene ether radical selected from the group consisting of $-(CH_2)_2-O-(CH_2)_2-$ and $-(CH_2)_2-O-(CH_2)_2-O-(CH_2)_2-$ (abbreviations DEG and TEG), with the remainder being selected from the group consisting of ethylene ($-(CH_2)_2-$ and abbreviation 2G), $-(CH_2)_3-$ (abbreviation 3G) and $-(CH_2)_4-$ (abbreviation 4G).

Other embodiments of the invention include fibers, films and coatings of the above polyesters and nonwovens of the fibers. The invention also contemplates disposable products, such as diapers, which contain an absorbent body portion, with, on at least one surface, a water permeable nonwoven sheet composed of the polyester fibers, a water impermeable film of the polyester, or a combination thereof.

It is a finding of the invention that such polyesters derived from terephthalic acid (abbreviation T), a metal salt of a 5-sulfoisophthalic acid (abbreviation 5SI), ethylene glycol (abbreviation 2G) or other lower alkylene glycol (such as 3G and 4G), polyethylene ether radical (abbreviations DEG or TEG) and a $C_2$-$C_4$ polyalkylene glycol radical of the indicated molecular weight undergo degradation when subjected to the conditions of high humidity and temperature that typically characterize composting operations. It is also significant that the bulk of the monomers resulting from degradation, i.e. terephthalic acid and the glycols, are readily digested by organisms in solid waste or compost to create carbon dioxide and water.

A preferred polyester of the invention is that indicated by the abbreviation (II) 2G/PEG (91-94/15-20W)-T/5SI(98-98.5/1.5-2) where the numbers connote the mole percentages of the diacid monomeric units in the polyester, with the PEG content being denoted in weight (w) % of the total polymer, and the 2G constitutes the remainder of the "G" content. Such abbreviations to connote compositions on a mole % basis (except for the polyalkylene glycol content) will be used throughout this specification.

These polyesters provide useful materials having applications in end uses where containment of body fluids is necessary and disposability is desirable in a degradable film or a fabric coated with a film which will conform easily to body contours yet act as an effective barrier to penetration of body fluids. It is especially preferred that such a film or coated fabric should have a reduced tendency to rattle and rustle when flexed during body movements. Such a film or fabric must have adequate strength and toughness to allow its survival during use. In order that it not leave objectionable residues when disposed of, it should disintegrate quickly when placed in proper waste disposal facilities and, ultimately, degrade substantially completely to innocuous materials, such as carbon dioxide and water.

Many copolyesters which are copolymerized with 5-sulfoisophthalic acid (5SI) will hydrolyze readily. Not all such copolymers are acceptable in the end uses contemplated. The polymers should exhibit the desired physical properties, and be processable under practical conditions, but the products of hydrolysis should desirably have the potential to be digested by the organisms likely to be found in waste disposal facilities and compost. This cannot be achieved by all monomers used in preparing other copolyesters. We have found, for example, that terephthalic acid is decomposed substantially completely in such a test over 28 days, and that ethylene glycol, and polyethylene glycol with MW 600 and 1000 are also satisfactorily digested by organisms typical of those found in waste disposal systems; typically, as the molecular weight increases, degradation generally becomes slower. Sodium dimethyl 5-sulfoisophthalate shows very slow degradation in these tests, but it constitutes a very small proportion of the copolymers of the invention.

According to a further aspect of the invention, the polyesters may be copolymerized carefully to provide copolyesters containing, by weight of the copolyester, about 60%-98% of (1) the above polyester(I) with about 2% to 40% consisting essentially of structural units (2) of the formula $[-C(O)-Q-O-]_n$, wherein n is an integer, and wherein Q is such that the hydroxy acid HO—C(O)—Q—OH and/or the polyhydroxy acid HO[—C(O)—Q—O—]$_n$H has a melting point at least 5° C. below its decomposition temperature, and Q is preferably $-CH_2-$, $-CH_2-CH_2-$, $-CH_2-CH_2-CH_2-$, $-(CH_2)_5-$, $-C(R')H-$, or $-C(R')H-CH_2-$, where R' is selected from the group of $-CH_3$ and $-CH_2-CH_3$, similar to the copolyesters more fully described in copending application Ser. No. 07/645,995, filed by Tietz simultaneously herewith.

DETAILED DESCRIPTION OF PREFERRED EMBODIMENTS

The polyesters of the invention consists essentially of recurring structural units of Formula I

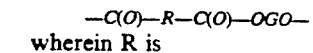

wherein R is about 97 to 99.9 mole % T (para-phenylene) and about 0.1 to 3 mole % of 5SI (i.e., a radical)

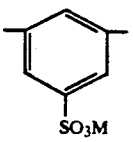

where M is
an alkali metal or alkaline earth metal, and
wherein G is
at least about 13 % by weight of a radical of a polyalkylene glycol of MW at least about 250,
up to about 40 mole % of a polyethylene ether radical selected from the group consisting of —(CH$_2$-)$_2$—O—(CH$_2$)$_2$— and —(CH$_2$)$_2$—O—(CH$_2$-)$_2$—O—(CH$_2$)$_2$—, respectively, DEG and TEG,
with the remainder being selected from the group consisting of C$_2$-C$_4$ lower alkylene groups, such as 2G (ethylene), 3G and 4G.

The polyesters of the invention are water-insoluble, unlike other polyesters which might be derived from the same constituents but which contain very much higher mole percentages of 5SI. They also have relatively low glass transition temperatures, Tg.

Thus, advantageously the Tg of the polyester fibers or films should be no higher than approximately the temperature at which degradation will take place. Since the temperatures in composting operations are often no higher than about 70° C., it is desired that the Tg of the polyester be no more than about 70° C., preferably about 65° C. or below. Commercial unmodified polyethylene terephthalate (abbreviation 2GT) polyester fibers have a Tg of about 80° C. Even a 2G-T polyester containing 2.5 mole % of 5SI has a Tg value of 76° C.

As indicated, the molecular weight (MW) of the polyalkylene glycol should be relatively low, a polyethylene glycol of MW about 600 being satisfactory and generally preferred, as it is available at a reasonable cost, which is an important consideration for many end uses. Molecular weights that are higher, such as 3500, are reputedly biodegradable, but are not so easy to handle, so are generally less preferred, and may not be so available. Polypropylene glycol is not as desirable as polyethylene glycol.

The desirable amount of polyalkylene glycol is generally at least 13% by weight, depending on the MW of the polyalkylene glycol used. 13% by weight corresponds to about 6 mole % when the MW is 600. Amounts of about 13 to 20% by weight, preferably 15%-20%, have proved satisfactory. We have found that smaller amounts of polyalkylene glycol, such as 8% by weight, do not appreciably increase toughness, as shown (8 w%) in Table 5, hereafter. These amounts are all based on the total G content of the polymer. Use of a significant amount of DEG or TEG will generally affect the amount of polyalkylene glycol that is desirable. Since polyalkylene glycols, including PEG, are relatively expensive, as compared with 2G, DEG, or TEG, and cost is an important consideration, it will generally be preferred to avoid using more polyalkylene glycol than required, and to use DEG (or TEG), if desirable. Amounts up to 75% by weight of polyalkylene glycol may be used, however, bearing in mind the increased cost.

It will be understood that with minor variations in composition, it is possible for the polyesters of the invention to have a further significant reduction in their Tg values. For example, the replacement of up to 5 mole % of the terephthalic acid with an aliphatic acid such as azelaic, succinic, adipic, sebacic or glutaric acid, and the replacement of some of the ethylene glycol with a polyethylene ether, such as DEG or TEG (triethylene glycol) can lower the Tg even below 65° C. Such amounts will not otherwise materially alter the degradation characteristics of the polyesters, hence their inclusion is contemplated by the term "consisting essentially" used to describe the polyesters and other products of the invention.

Minor amounts of polyfunctional branching agents, such as trimellitic acid residues, may be incorporated to modify melt rheology and film processing, if desired.

The polyesters of the invention may be prepared by conventional polycondensation techniques using, for example, as the glycol component, a combination of about 15% to 20% by weight of the polyalkylene glycol, with a complemental molecular amount of ethylene glycol, and, as the acid component, a combination of about 97 to 99.9 mole % of terephthalic acid with about 0.1 to 3 mole % of a metal salt of 5-sulfoisophthalic acid. Optionally up to about 5 mole % of the ethylene glycol or terephthalic acid can be replaced, respectively, by another glycol or by an aliphatic acid. In lieu of the mentioned dicarboxylic acids, ester forming derivatives such as the dimethyl esters of the acids may be used.

The glycol component may advantageously contain a polyethylene ether radical, such as DEG or TEG as well as the PEG and 2G to achieve an optimum level of degradability without a major sacrifice to fiber and film physical properties such as tensile strength. Above about 40 mole % DEG such properties are adversely affected, as indicated by Tietz.

The acid component is preferably about 1.5 to 2 mole % 5SI. This component is not only relatively costly but also excessively large amounts can render the polyesters water soluble and thus affect the fiber and film physical properties such as shrinkage. As little as 0.1 mole % of the 5SI contributes significantly to the degradability characteristics of the resultant fibers and films.

In the 5SI monomeric units, the metal ion is preferably an alkali metal such as sodium, potassium or lithium. However, alkaline earth metals such as magnesium are also useful. A 5-sulfoisophthalate that has given very good results is the sodium salt.

A relative viscosity of at least 16, preferably at least about 18, is generally acceptable for melt spinning performance.

In the Examples herein, the various monomeric components are charged to a polymerization vessel along with an antimony or other catalyst and subjected to polycondensation conditions to produce a linear polyester in which the units are randomly distributed along the molecular chain. It will be understood that it is also possible, however, to first react two or more of the monomeric components to a prepolymer stage, followed by addition of the remaining components which may be polymeric such as polylactide, polyglycolide or polycaprolactone and completion of the polymerization.

The polyesters of the invention are very hydrolytically sensitive, having a higher equilibrium moisture content than 2G-T resin and a faster moisture regain rate. It is desirable that isolated flake be dried thoroughly, preferably to a moisture content below 400 ppm before reextrusion, and to maintain a nitrogen atmosphere around all possible air in leakage points, and to transfer polymer in warm condition (e.g., above about 50° C.) from the dryer to the extruder.

The polyesters as isolated from the reactor usually have multiple melting points by DSC analysis. These are seen at temperatures which overlap those which might be used in drying 2G-T flake, making it difficult to dry these polymers without fusing the flake into a solid mass when they are rapidly heated to get fast economical drying rates. Slower heating to allow crystallization, after which heating at higher temperatures for fast drying, is desirable.

A desirable procedure for preparing high molecular weight resins from rapidly polymerized lower molecular weight ones may be to use solid phase polymerization of low molecular weight flake. This procedure may desirably be carried out after or in combination with the crystallization procedure mentioned above so that temperatures high enough for rapid polymerization can be attained without fusing of the flaked resin. In addition, as known from U.S. Pat. No. 3,544,523, anticaking agents may be useful to prevent sticking, such as Cab-o-sil grade MS-75D, and other finely divided inert solids, like $TiO_2$, talc, carbon black and clay.

If it is desired, for environmental or other reasons, to avoid use of a catalyst that comprises antimony or another heavy metal, then this may be achieved, for instance, by using a crystalline sodium aluminosilicate molecular sieve such as Linde Molecular Sieve 13X, type 9356, with a nominal pore size of 10A, obtained from Union Carbide Corporation. Such procedure is more fully described in commonly assigned U.S. application Ser. No. 07/497,069 filed Mar. 20, 1990 in the name of Jackson, but other methods of avoiding antimony may be used, if desired.

In any event, the particular mole percentages of the aforementioned components are desirably selected to provide a polyester which in fiber or film form has a Tg of 70° C. or less, preferably of about 65° C. or less.

As will be understood, while the polyesters of the invention are well suited for use as fibers or filaments in nonwoven sheets, they can be used to particular advantage in the form of cast and blown films, coatings, or molded articles wherever polyesters with such properties are desired.

Fibers and filaments herein are interchangeable terms in the general sense, but where a more specific acknowledgement of length is appropriate, the term "fibers" is intended to refer to short filaments as in "staple fibers". Hereafter only one of the terms may be used.

The polyesters of the invention may be converted to fibers or filaments by conventional melt spinning techniques. Deniers of 1 to 15 dpf are most common. The filaments may be used as-spun(undrawn) or in a stretched (drawn or oriented) condition. Drawing to reduce denier or for increasing orientation can be accomplished by the usual procedures.

The polymer compositions of the invention can be formed into nonwoven fabrics via a number of processes. These may be roughly divided into spunbonded fabrics and those fabrics using staple fibers. These are discussed in "Encyclopedia of Textiles, Fibers and Nonwoven Fabrics", Ed. Martin Grayson, John Wiley and Sons, New York, 1984, pp 252-304. The compositions described herein can be used in many such products. Spunbonded nonwovens can be prepared by spinning and laying down simultaneously into webs of continuous filaments using known methods of distributing the threadline in the desired orientation in the web plane. Such webs can be thermally bonded under suitable conditions of time, temperature and pressure to strong fabrics with tensile properties which are usually superior to those obtained with staple webs. Bonding can also be carried out by using suitable adhesives and both these methods may be used to make point bonded or area bonded fabrics. Needle punching may also be used to give the webs stability and strength. Spunbonded fabrics can also be made by melt blowing wherein a stream of molten polymer is extruded into a high velocity stream of heated air and a bonded web formed directly on a screen conveyor from the resultant fibers. Nonwoven fabrics can also be made by direct extrusion through a rotating die into a netlike product (U.S. Pat. No. 3,959,057 J. J. Smith) or by stretching and drawing embossed films of the thermoplastic polymers (British Patent 914,489 and 1,548,865 to Smith and Nephew Research Ltd.).

Staple fibers can be made into nonwovens by several processes. Most of these can be classified into (1) web preparation and (2) reinforcing ("Manual of Nonwovens", Dr. Radko Krcma, Textile Trade Press, Manchester, England, pp 74-76, 1971). During web preparation, bales of staple fiber are opened and formed into a web having either a random orientation (via air, water or electrostatic deposition) or parallel or crosslaid orientation (via carding and plying). Reinforcement to impart physical integrity and useful mechanical properties can be accomplished by mechanical means such as needlepunching or hydroentanglement (where water jets move fibers out of the plane of the web and entangle them) as in the spunlaced fabrics (U.S. Pat. No. 3,485,706 to Du Pont) or by stitchbonding where a reinforcing thread is sewn through the web. (See "Principles of Stitch Through Technology" Nonwovens Fabrics Forum, Clemson University, Clemson, SC, 1978 by J. D. Singelyn). Reinforcement can also be accomplished by adhesive bonding which includes impregnation of the web by a water based resin binder solution or dispersion and subsequent evaporation of the water leaving a fabric which is composed typically of 60%–70% by weight fiber and 30%–40% by weight binder. Dry adhesive powders may also be applied to the staple web prior to a heating step to produce a powder-bonded nonwoven. Webs of thermoplastic staple fibers may also be reinforced by thermal bonding in which use is made of the ability of the fibers to soften and adhere to each other upon application of heat. As with the spunbonded fabrics these may be point bonded or area bonded. Heat may be applied by hot air (known as through air bonding) or by a pair of patterned and/or flat heated rollers which form a nip through which the web passes to achieve bonding. This process may be carried out with 100% thermoplastic fibers or with blends of thermoplastic fibers with fibers which do not thermally bond in the 100% form, i.e. cotton and rayon.

In addition, useful articles can also be made by laminating, extrusion melt coating or adhesively combining the above types of nonwoven fabrics with each other, with films or staple webs in such a way as to confer desired properties on the combined fabric.

In particular, a fabric made by extrusion melt coating a thin, pinhole free film of the compositions of this invention on a nonwoven, made by the spunbonded process or by thermally bonding staple from fibers of this invention alone or in combination with other compostable fibers such as cotton or rayon, is aesthetically pleasing and non-fluid permeable.

The compostable polyester fibers described herein may be used in all these methods of preparing nonwovens to yield fabrics which when subjected to composting conditions will be substantially degraded. Thus staple webs of the polyester fibers, as well as blends of these fibers with cotton and rayon, may be bonded by hydro-entanglement, by needle punching, by wet resin bonding and by dry adhesive bonding. (The adhesives used should be chosen to allow the desired degradation under composting conditions.)

Thermally bonded staple webs of the described compostable polyester fibers can be made in the 100% form or webs containing a significant proportion of these fibers together with cotton and/or rayon may be thermally bonded to fabrics having useful mechanical properties.

Continuous or spun yarns prepared from the compositions described herein may be used to stitch bond webs of fibers such as cotton, rayon or blends of these fibers, or wood pulp, with the compostable polyester fibers of this invention resulting in fabrics which will degrade under composting conditions.

Spunbonded fabrics can be made by thermally bonding webs of continuous fibers prepared from the compostable polyester compositions described herein and by blow spinning, direct extrusion to nets and drawing of embossed films.

The compostable compositions described herein can be melt extruded as films to coat spunlaced nonwoven fabrics which themselves may be composed of compostable fibers alone or in combination with wood pulp, rayon or cotton.

Nonwoven webs of the compostable compositions made by the melt blowing process may also be used as an adhesive layer between other nonwoven fabrics.

It is apparent that the fiber, film, and sheet products made from compositions described herein have a great number of applications in products which are disposed of or potentially may be disposed of in composting systems. In addition the compositions have utility in objects made by injection molding, injection blow molding, thermal forming of sheets, rotational molding of powder, extrusion, and pultrusion, which desirably can be disposed of an degraded in composting systems. The following is a nonexclusive list of such and uses:

Agricultural mulch
Agricultural mats containing seeds, nutrients
Adhesive tape substrate
Baby pants
Bags
Bag closures
Bed sheets
Bottles
Cartons
Disposable diapers
Dust bags
Fabric softener sheets
Garment bags
Garbage and lawn waste bags
Industrial bags
Labels, tags
Monofilaments
Packaging films and structures
Pillow cases
Protective clothing
Surgical drapes
Surgical gowns
Surgical sheets
Surgical sponges
Tampon applicators
Temporary enclosures
Temporary siding
Toys
Wipers.

The invention can provide fluid impermeable sheets which are compostable in typical waste disposal facilities. Preferably these sheets should not rattle or rustle objectionably and should have strength and toughness adequate for use in personal absorbent products, such as disposable diapers.

The fibers, films and nonwoven fabrics prepared from the compositions of the present invention are of particular utility in disposable diapers since in that use they have an enhanced capability of being degraded in a composting operation. Typical examples of disposable diaper constructions are given in U.S. Pat. No. 3,860,003 (Buell) and U.S. Pat. No. 4,687,477 (Suzuki et al.), the disclosures of which are incorporated herein by reference. The items which can be made of the compostable compositions of this invention are (1) the backsheet film, i.e., the water-impermeable outside layer, which may be a film which is 100% of the compostable composition or it may be a laminated sheet with a nonwoven or web of compostable fibers including cotton or rayon adhered to the film, (2) the topsheet, i.e., the water-permeable or inner layer, which is a nonwoven fabric of the compostable fiber composition or a blend of the compostable fiber of this invention with cotton or rayon fiber having a porosity suitable for passing urine quickly to the fluid-absorbing pad between the topsheet and backsheet film, and (3) the fastening tapes which may optionally be made from films or nonwovens of the compositions of the invention. The fastening tapes are typically coated with a pressure sensitive adhesive.

It will be apparent that the products of the invention may contain additives such as dyes, pigments, fillers, etc.

TEST METHODS

Polyester glass transition temperatures. $T_g$, are obtained by using a Du Pont model 2910 Differential Scanning Calorimeter. Samples are heated under a nitrogen atmosphere at a rate of 20° C./min to a temperature 10° C.–20° C. above the melting point, then the melt is cooled using the rapid air quench capability of the instrument. The $T_g$ is determined from the second cycle scan done at 20° C./min. using the internal software to determine the inflection point of the baseline shift.

Polymer melting point, m.p., is determined on the first heating cycle as described in $T_g$ determination. The temperature at which the highest endothermic peak occurs is reported as the polymer melting point.

Number average molecular weight, $M_n$, is determined by gel permeation chromatography (gpc) versus a standard polyethylene terephthalate sample with an $M_n$ of 22000 and a weight average molecular weight of 44000. Polymers are dissolved in and the analysis is run using HFIP (hexafluoroisopropanol) containing 0.01 M sodium trifluoroacetate as the solvent. A Waters model 150C ALC/GPC instrument, or its equivalent, is used with two Zorbax PSM-S biomodal columns (sold by E. I. du Pont de Nemours and Company) (or equivalent) in series at 30° C. A refractive index detector was used and data collected at 100 intervals and analyzed via software provided by the instrument supplier.

Carboxyl end groups are determined by titration of an o-cresol solution of the polymer at 115° C. with KOH in benzyl alcohol to a colorimetric endpoint using bromophenol blue as the indicator. Results are reported in eq./$10^6$ grams of polymer.

Inherent viscosity is defined in "Preparative Methods of Polymer Chemistry", W. R. Sorenson and T. W. Campbell, 1961, p. 35. It is determined at a concentration of 0.5 g/100 ml of the indicated solvent at the indicated temperature, usually HFIP at 30° C.

Tensile Properties of fibers and yarns are coded as T/E/M/To for tenacity, elongation, initial modulus, and toughness and are reported in their conventional units of grams per denier, percent, grams per denier, and grams per denier. These are measured on conditioned samples (3 inch guage length) in a commercial testing machine at the rate of extension of 50% per minute (unless otherwise indicated). Toughness(To) is measured as the integrated area under the stress-strain curve. The counterpart properties of fabrics are similarly coded as T/E/M/To and are reported in units of lb./in./oz.sq.yd., percent, lb./in./oz./sq.yd., and lb./in.-/oz.sq.yd., respectively. Fabric samples are 1 inch ×8 inches (with 5 inches guage length), are conditioned prior to testing, and are extended in a commercial testing machine at a rate of 100% per minute.

Relative viscosity is the ratio of the viscosity of a solution of 0.8 gram of polyester dissolved in 10 ml of hexafluoroisopropanol (HFIP) containing 80 ppm $H_2SO_4$ to the viscosity of $H_2SO_4$- containing HFIP itself, both measured at 25° C. in a capillary viscometer and expressed in the same units.

Crimp index is measured by straightening a crimped tow by application of about 0.1 gpd load. Then 0.5 gm clips 66.6 cm apart are attached to the extended tow. The tow is then cut 11.2 cm beyond each clip to give a sample of 90 cm extended length. The sample is suspended vertically, hanging freely from one of the clips to allow retraction to crimped length. After about 30 secs., clip-to-clip distance is measured.

$$\text{Crimp Index} = \frac{(66.6 - Lc)}{66.6} \times 100$$

where Lc is the clip-to-clip distance in the free-handing state.

Crystallinity index is measured by first obtaining a diffractogram as described by Blades (U.S. Pat. No. 3,869,429, col. 12) with some modifications. The high intensity X-ray source is Phillips XRG-3100 with a long fine focus copper tube. Diffraction is analyzed with a Phillips single axis goniometer equipped with a theta-compensating slit and a quartz monochromator set to exclude copper $K_b$ radiation. Diffracted radiation is collected in step scanning mode in 0.025 steps with a 1.5 sec. per step count time. The digital data so collected are analyzed by a computer and smoothed by a running fit to second order polynomial. The computer is programmed to define a straight base line which joins the diffractogram tangentially at about 113 and 343. Crystallinity index is defined as $$\frac{A \times 100}{A - B}$$

where A is the intensity of the 18° 010 peak above this base line and B is the intensity of the 20° minimum above this base line. Crystallinity index has been related to percent crystallinity determined by density (see U.S. Pat. No. 4,704,329, col. 8, 9). Weight percent crystallinity=0.676 ×Crystallinity index.

The invention will be further illustrated by the following Examples wherein parts and percentages are by weight unless otherwise indicated, and the polymer compositions are generally mole %, except for the PEG, being by weight (w), using the same abbreviations for DEG, PEG and for 5SI, with the remaining glycol being 2G, and the remaining diacid being T. The "Hydryolsis" results are generally after boiling in water at 100° C. for 24 hours, except as indicated, e.g. in Example 4, and show reductions in molecular weight (Mn), as percentages.

EXAMPLE 1

This Example shows the laboratory preparation of a hydrolytically degradable copolyester, its use in extrusion coating of a thermally bonded non-woven fabric made from hydrolytically degradable fibers prepared according to copending patent application Ser. No. 07/522,134 (Tietz, referred to above), and the physical degradation of the copolyester by hydrolysis and composting.

COPOLYESTER RESIN

The copolyester resin for coating is made to have the following composition:
PEG (MW 600) 14% by weight (about 5.7 mole %)
5 mole % DEG
89 mole % 2G
2 mole % 5SI
98 mole % T.

Some deviation in composition may result from generation of DEG as a byproduct during polymerization and its incorporation in the copolymer in minor amounts.

In a 35 gallon reactor containing a stirrer, a nitrogen inlet and a distillation column are placed:
39372 grams dimethyl terephthalate (DMT)
24358 grams ethylene glycol (2G)
1134 grams diethylene glycol (DEG)
7031 grams (MW 600) PEG
1229 grams 5SI dimethyl ester
9.1 grams Na(OAc)·$3H_2O$
41 grams $Sb_2O_3$
29 grams Mn(OAc)$_2$·$4H_2O$.

The temperature of the reactor is slowly increased. Distillate (methanol) is collected in the amount of 11600 ml between 160° C. and 213° C. A second distillate (ethylene glycol) in the amount of 6300 ml is collected between 224° C.-240° C. The resultant oligomer is transferred to a second vessel containing an agitator and vacuum capabilities. Then 20 g of 85% phosphoric acid is added to the transferred material, the temperature raised to 273° C. and the maximum vacuum (0.5 mm Hg) is established over 90 minutes. After 2.5 hours at these conditions, the contents of the reactor are discharged through a ribbon die into a water quench. The yield of polymer is 91 lb. with an inherent viscosity of 0.84 (HFIP @30° C.). The ribbon is cut to flake and dried at 60° C. overnight in a vacuum tray dryer with a vacuum between 1 and 2 mm Hg and a nitrogen purge.

The coating resin has melting points of 105° C. and 215° C. by DSC. Its recrystallization and drying was achieved by placing 85 pounds of the resin in a Patterson Kelley double cone vacuum dryer model 124, establishing about 2 mm Hg absolute vacuum, rotating the dryer at 6 rpm and slowly heating the system to 150° C. oil temperature. The temperature of the oil is raised in steps with sufficient time at each step for the polymer temperature to reach equilibrium with the oil. A sequence of temperature increases that has been found useful is 60°, 75°, 100°, 135° and 150°0 C., with sufficient time at each temperature to permit the resin to reach thermal equilibrium with the heat transfer oil. The resulting resin has melting points by DSC of 160° C. and 215° C.

FABRIC FOR COATING

The nonwoven fabric for coating is prepared from 1.5 dpf, 1.5 inches long staple fibers with a composition of 80 mol % 2G/20 mole % DEG - 98 mole % T/2 mole % 5SI prepared by extruding polymer at a rate of 475 cc/min through 900 orifices of about 0.38 mm diameter at 275° C. into 21° C. quench air to form filaments which are taken up at a speed of about 1625 yards/min. About 0.2% spin finish is applied (3.5% water emulsion of a mixture of an anoinic surfactant "Zelec" NK from E. I. du Pont de Nemours and Company and a nonionic lubricant "Nopco" 2152P from Henkel Co.) to the yarn bundle. Bundles of filaments are collected to form a tow of about 490,000 filaments which are drawn at a draw ratio of 2.83 ×at 36° C. in water. The fibers are crimped in a stuffer box crimper and heat treated at 133° C. for about 10 minutes. The fibers have a tensile strength of 2.6 gpd (extension rate was 40% per minute), a 160° C. dry heat shrinkage of 8%, and a crimp level of 12 crimps/in. The melting point of the fiber is 207° C.

The fiber is converted to thermally bonded fabric on a conventional card non-woven line. First it is carded into three 9-10 g/yd$^2$ webs which are combined and drafted to a 25 h/yd$^2$ web which is passed at 200 m/min through the nip of a calender having two male rolls, heated to 345° F. to bond the fibers and give a 25 g/yd$^2$ basis wt. fabric with an average cross direction tensile of 230-250 g/linear inch and a machine direction strip tensile of 1000 g/linear inch.

COATING THE FABRIC

The recrystallized coating resin is placed in a hopper above the inlet of a 1 inch extruder (Echlin Mfg. Company, Serial #0717) with an 18 inch wide film die with a 0.007 inch gap. The width of the die was reduced with plugs to 17 inches to accommodate the width of the fabric being coated, 16 inches.

The fabric for coating is led continuously at different speeds, varying from 47-106 ft/min through an extrusion coating machine made by Bertek, Inc. of St. Albans, VT (their own design). The fabric is led through a corona treatment (made by Intercon) through an S-wrap between two 4 inch diameter rolls heated to 150° C.-260° F. on to a polytetrafluoroethylene-coated, matte-finished chill roll at 100° F.-200° F., around 300 degrees of the circumference of this 12 inch diameter roll, while the coating resin is extruded through the 17 inch wide die at a delivery rate of 83 cc/min (20 rpm when run at 49.6 ft/min.) at a position between the chill and in rolls as close as possible to the chill roll (about 0.25-0.5 inch). The temperature of the extruder and die can range from 430° F.-460° F. A film with 0.5 mil thickness was applied to the fabric. The extrusion-coated fabric has a basis wt. of 1.1 oz/yd$^2$, a machine direction strength of 3.9 lb/in/oz/yd$^2$, a toughness of 0.72 lb/in/oz/yd$^2$ and a breaking elongation of 22%. The fabric exhibited a desirable softness and the substantial absence of a rustling sound when flexed. When the barrier (film-coated) side of this fabric is coated with a water of isopropyl alcohol solution of red dye, no penetration is noted.

When a sample of this fabric is boiled in water for 24 hours, it disintegrates into loose short brittle fibers, white particles and powder.

When samples of this fabric are placed in a 30 gallon rector filled with municipal solid waste seeded with sewage sludge taken from a municipal waste composting facility, it decreases an average of 69% in tensile strength after 6.5 days exposure, during which time a temperature of at least 65° C. is maintained. The final moisture content is 47.3%.

In place of the resin recrystallization described above, an alternate procedure for preparing a suitable coating resin is to subject a lower molecular weight resin to solid state polymerization to obtain a higher molecular weight resin. For example, a 75 g. sample of an unrecrystallized resin of the same composition as the coating resin used above, and having an inherent viscosity of 0.80 (in HFIP), is placed in a "BUCHI" Rotovapor model RE120 rotary evaporator fitted with a 500 ml round flask modified to encourage agitation of flake. Vacuum is established at or below 1 mm Hg absolute, rotation is carried out at 10 rpm and the contents of the flask are slowly heated from room temperature to 195° C. for 3 hours. The solid phase polymerized resin has an inherent viscosity of 0.94 and a single DSC melt point of 228° C.

A similar extrusion-coated fabric (same fiber composition as above) was made using a resin with the composition 2G/PEG(94/14w)-T/5SI(98/2) with an inherent viscosity of 0.87 (30° C. in HFIP). The coated fabric, with a basis weight of 1.3 oz/yd$^2$, had T/E/M properties of 2.8/3/125 in the machine direction and 1.4/2/73 in the cross direction (T and M being lb/in/oz/yd$^2$). The fabric, with a 0.5 mil thick coating, showed relatively low noise generation (rustling) and enough toughness and adhesion to prevent bursting and delamination when pulled by hand at low tension in the cross machine direction. When boiled in water for 24 hours, the fabric was reduced to small particles, powder and loose fibers.

EXAMPLE 2

This Example shows degradable extrusion-coated spunlaced non-woven fabrics and a process for their preparation.

The spunlaced non-woven fabrics are made by the teachings of U.S. Pat. No. 3,485,706, using the degradable fibers described in Example 2 of the copending parent Tietz application. Fabric A consists of 100% degradable staple fiber which has a dpf of 2.6, 12 crimps/in. and is cut to a length of 2.2 cm. It had tenacity/elongation of 1.3 gpd/67%. It is carded into a 1.3 ox/yd$^2$ web by an air-laydown process of the type described in U.S. Pat. No. 3,797,047. Then in a continuous operation, the web is carried by a screen and forwarded at a speed of 50 m/min past a series of banks of water jets under the conditions shown in Table A, around a drum screen where a second series of banks of water jets treats the back side of the web. This fabric A has a basis weight of 1.3 oz/yd² with grab tensile and elongations in the machine direction (MD) of 10.3 lb/oz/yd² and 73.5% and in the cross direction (CD) of 8.1 lb/oz/yd² and 138% (ASTM method D1682).

TABLE A

| Jet Bank No. | Orifice dia. in(mm) | # Jets/ in.(cm) | Pressure psi | Pressure kPa |
|---|---|---|---|---|
| 1 | 0.004(0.102) | 40(15.7) | 528 | 3640 |
| 2 | 0.005(0.127) | 40(15.7) | 740 | 5110 |
| 3 | 0.005(0.127) | 40(15.7) | 1057 | 7290 |
| 4 | 0.007(0.178) | 20(7.9) | 1242 | 8570 |
| 5 | 0.007(0.178) | 20(7.9) | 1490 | 10280 |
| Drum Screen Jets | | | | |
| 1 | 0.005(0.127) | 40(15.7) | 586 | 4040 |
| 2 | 0.005(0.127) | 40(15.7) | 586 | 4040 |
| 3 | 0.005(0.127) | 40(15.7) | 845 | 5830 |
| 4 | 0.005(0.127) | 40(15.7) | 0 | 0 |
| 5 | 0.005(0.127) | 40(15.7) | 1535 | 10590 |
| 6 | 0.005(0.127) | 60(23.6) | 1385 | 9560 |

Fabric B consists of 50 wt % degradable fiber and 50% wood pulp. It is made by forming a 0.9 oz/yd² air laid web as described for Fabric A; then, in a continuous operation, carrying this web on the same type of screen as in A, at a speed of 60 m/min together with a continuous sheet of Harmac paper under banks of jets operating at the conditions in Table B. No jet treatment of the back of the sheet was carried out. Fabric B has a basis weight of 2.2 oz/yd², with grab tensiles and elongations in the MD of 16.2 lb/oz./yd² and 27% and in the CD of 14.2 lb/oz/yd² and 79% (ASTM method D 1682). It is asymmetrical with a high wood pulp side and a high degradable polyester side.

TABLE B

| Jet Bank No. | Orifice dia. in(mm) | # Jets/ in.(cm) | Pressure psi | Pressure kPa |
|---|---|---|---|---|
| 1 | 0.005(0.127) | 40(15.7) | 89 | 610 |
| 2 | 0.005(0.127) | 40(15.7) | 157 | 1080 |
| 3 | 0.005(0.127) | 40(15.7) | 704 | 4860 |
| 4 | 0.007(0.178) | 20(7.9) | 1157 | 7980 |
| 5 | 0.005(0.127) | 40(15.7) | 0 | 0 |
| 6 | 0.005(0.127) | 40(15.7) | 1096 | 7560 |

The fabrics are coated using the resin with composition 2G/PEG(94/14w-T/5SI(98/2) described in Example 1 with the same machine as described in Example 1. The 1 mil coatings are made at an extrusion speed of 230 cc/min and a windup speed of 65 ft/min. The 0.5 mil thick coatings are made at 166 cc/min and 94 ft/min. The properties of the coated fabrics are in TABLE 1.

TABLE 1

| Fabric | Thick. (mil) | Basis Wt. oz/yd² | T/E/M/To MD/XD |
|---|---|---|---|
| A | 0.75 | 1.5 | 3.8/60/75/1.8 |
| | | | 1.8/130/32/1.5 |
| B | 0.5 | 1.6 | 2.3/60/88/0.99 |
| | | | 1.1/141/47/0.79 |
| B* | 1.0 | 3.5 | 3.7/7/148/0.18 |
| | | | 2.3/61/88/1.3 |
| B* | 0.75 | 2.9 | 3.6/12/143/0.36 |
| | | | 2.1/61/60/1.1 |
| B* | 0.5 | 2.8 | 3.6/16/129/0.50 |
| | | | 2.0/60/46/0.91 |
| B** | 1.0 | 3.6 | 3.6/3/228/0.07 |
| | | | 2.0/92/107/1.64 |
| B** | 0.75 | 2.9 | 2.7/19/154/0.44 |
| | | | 1.7/72/62/0.92 |
| B** | 0.5 | 2.7 | 3.2/13/204/0.37 |

TABLE 1-continued

| Fabric | Thick. (mil) | Basis Wt. oz/yd² | T/E/M/To MD/XD |
|---|---|---|---|
| | | | 2.0/85/71/1.30 |

*High polyester side
**High Wood Pulp side

When Fabric B was boiled in water for 24 hours, the $M_n$ of the polyester film and coating was reduced by mole than 80%.

EXAMPLE 3

This Example shows the preparation of two copolyesters of the invention in film form and their hydrolytic degradation. The polymers are made by the general procedure described below. Some deviation in DEG content may result from distillation during polymerization.

In a 500 cc, 4 necked resin kettle fitted with a mechanical stirrer, condenser, distillation head with receiver flask, and a capillary $N_2$ inlet tube are placed:

81.8 g ethylene glycol
63.0 g polyethylene glycol (MW 600)
8.5 g diethylene glycol
0.138 g Mn(OAc)$_2$·4H$_2$O (150 ppm)
0.074 g Sb$_2$O$_3$.

This is warmed to 160° C. to bring the contents of the flask into solution and 142.8 g Dimethyl terephthalate
3.51 g sodium salt of dimethyl-5-sulfoisophthalate are added and the temperature gradually raised to 230° C. while methanol distillate is collected. Then 0.5 ml of a H$_3$PO$_4$ solution (4.79 g of 85% H$_3$PO$_4$ diluted to 50 ml with ethylene glycol) is added. The resultant molten monomer is poured into a polymer tube to fill it about ⅔, a capillary inlet tube drawn to a fine point is inserted to reach the bottom of the tube and a filter flask attached to the sidearm of the tube to act as a receiver. Polymerization is continued by heating the tube in a dimethyl phthalate vapor bath (284° C.) first under laboratory vacuum for about 1 hour and then down to 0.35 mm Hg over 1.5 hours, then about 2 hours at 0.35 mm. The capillary is removed from the molten polymer and, after cooling, the polymer is recovered from the tube and ground into small particles in a Thomas mill. This flake is dried at 100° C.-130° C. under laboratory vacuum. It is pressed into the films evaluated below by pressing between polytetrafluoroethylene films at a temperature 5° C.-10° C. above the highest melting point determined by DSC.

Hydrolysis was carried out by placing a piece of film 1-2 mils thick, about 1 g, in 250 ml deionized water and boiling for 24 hours.

TABLE 2

| Composition DEG/PEG/5SI | Press T °C. | Initial $M_n$ | Hydrolysis % loss $M_n$ |
|---|---|---|---|
| 1) 10/29w/1.6 | 170 | 20260 | 47 |
| 2) 10/15w/1.6 | 180 | 26660 | 59 |

EXAMPLE 4

This Example describes the preparation and rapid hydrolysis of soft films of this invention by blow molding of three polymer compositions. The first was similar to what was used above, 2G/PEG(94/14w)-T/5SI(98/2).

There were also prepared films from 4G-T (instead of 2G-T) that include substantial proportions of polypropylene glycol capped with ethylene oxide (called "Thanol" E2103, MW=2100, from Texaco). These were hydrolyzed in water at 60° C. for 8 weeks in contrast to the 24 hour hydrolysis at 100° C. for item 1. Item 2 was made by the general procedure in Example 1, using 14 weight % (1.7 mole %) of the ethylene oxide capped polypropylene glycol (PO3), 2000 ppm tetrabutyl titanate ("Tyzor" TBT) as a catalyst, 0.1 mole % trimethyltrimellitate (TMTM) branching agent and a polymerization temperature of 250° C. for 45 min. at a vacuum of 0.8 mm Hg. Item 3 was made similarly, but 33 weight % (5 mole %) of the ethylene oxide capped polypropylene glycol and 0.2 mole % TMTM were used.

The apparatus used for blow molding the films consists of a ¾ inch Brabender extruder feeding a 1 inch diameter die with a 0.08 inch gap. The die is supplied in the center with an air feed which is maintained at a pressure which expands the extruded tube to a diameter of about 2.7 inch. The feed rate was about 40 cc/min for 1 mil thick film and about 80 cc/min for the 2 mil thick films. The blown film was wound up at about 25 ft/min.

TABLE 4

| Composition | Blow Molding T °C. | Hydrolysis | | |
|---|---|---|---|---|
| | | Init. Mn | Final Mn | % Mn Loss |
| 1) 2G/PEG-T/5SI (94/14w)-(98/2) | 235 | 47680 | 6005 | 87 |
| 2) 4G/PO3-T/5SI (98.3/14w)-(98/2) | 230 | 29145 | 6260 | 79* |
| 3) 4G/PO3-T/5SI (95/33w)-(98/2) | 215 | 25530 | 7910 | 69* |

EXAMPLES 5-9

These Examples show compositions which will give tough degradable materials such as films and coatings.

These polyesters are prepared by the procedure in Example 1 or by a procedure similar to that in Example 3. The MW of the PEG was again 600. The properties are evaluated by extruding the polymers at temperatures from the melting point to 10° C. above the melting point through a 0.009 inch diameter spinneret at a pump rate of 0.07 cc/min while the extrudate is wound up about 6 inches below the spinneret at wind up speeds from 7.5 to 38 m/min.

The properties are listed in Table 5 for fibers having a denier close to 30. Hydrolyses were carried out on some fibers (as indicated) wound up at 38 m/min, by boiling in water for 24 hours. Mn is determined by gpc. The compositions of Examples 5-9 of the invention show suitable toughness for use as extruded coatings and films. Each shows high toughness (To, integrated area under stress-strain curve in gpd) of at least 0.4 gpd. The test rate is 50% elongation/min.

In contrast, Comparisons C-H (made similarly, but with less PEG or without any PEG), did not show adequate toughness, usually much less than 0.01 gpd. Indeed, although Comparisons C, D and H had similar PEG (MW 600) in lower amounts than the Examples, their toughness was only comparable or even less than for Comparison F, without any PEG at all. This shows the importance of a threshold minimum amount of PEG, if a tough coating is desired.

TABLE 5

| Sample | Composition DEG/PEG/5SI | | | T/E/M/To gpd/%/gpd/gpd | | | | Mn | | |
|---|---|---|---|---|---|---|---|---|---|---|
| | | | | | | | | Init. | 24 Hr | % |
| Invention | | | | | | | | | | |
| 5 | 5 | 14w | 2 | .66 | 682 | 9 | 1.9 | | | |
| 6 | 0 | 15w | 1.6 | .42 | 507 | 24 | 1.44 | 36325 | 8235 | 77 |
| 7 | 10# | 14w | 1.6 | .22 | 701 | 5.4 | 0.75 | 48470 | 11650 | 76 |
| 8 | 10 | 29w | 1.6 | | Fused filaments | | | 63420 | 17430 | 73 |
| 9 | 6.5 | 17w | 2 | .45 | 684 | — | 0.45 | 49325 | 8415 | 83 |
| Comparisons | | | | | | | | | | |
| C | 0 | 8w | 1.6 | .13 | 1.6 | 15.7 | .0014 | | | |
| D | 15 | 8w | 1.6 | .25 | 3.7 | 10.8 | .0059 | 36725 | 8675 | 76 |
| E | 15 | 4w | 1.6 | .08 | 1 | 9 | .0002 | 27860 | 5870 | 79 |
| F | 24 | 0 | 3 | .36 | 2.8 | 18.3 | .0064 | | | |
| G | 10 | 4w | 1.6 | .29 | 2.6 | 14.2 | .0048 | | | |
| H | 10 | 8w | 1.6 | .30 | 2.1 | 15 | .0039 | 25270 | 7375 | 71 |

Notes:
TEG was used in Example 7
The last column shows the % loss of Mn over 24 hours.

EXAMPLE 10

This example shows the incorporation of polycaprolactone (6E) to give a copolymer 6E//2G-/PEG(600)(94/14w)-T/5SI(98/2)[14//86 wt %] which is tough and highly degradable by hydrolysis, essentially as described in application Ser. No. 645,995 filed simultaneously herewith.

The 2G/PEG(600)(94/14w)-T/5SI(98/2) polymer was made essentially as described hereinbefore:

72.2 g ethylene glycol
21.6 g polyethylene glycol (MW 600)
0.114 $Sb_2O_3$
0.092 g $Mn(OAc)_2 \cdot 4H_2O$
114.0 g Dimethyl Terephthalate
3.79 g Sodium salt of dimethyl 5-sulfoisophthalate.

After removal of methanol at temperature up to 220° C.
22.8 g of polycaprolactone
is added and stirring continued for 30 min. The molten product is transferred to a polymer tube as described in Ser. No. 07/645,995, and polymerization is continued while the tube is heated with a glycol vapor bath (198° C.) for 1 hour under laboratory vacuum and then for 20 hours under 0.3 mm Hg pressure. The polymer is cooled, ground and dried as in Ser. No. 07/645,995, then spun using a press spinning apparatus fitted with a 0.009 inch single hole spinneret at a temperature of 177° C. with a delivery rate of 0.7 cc/min and a windup speed of 38 m/min. These (38 m/min) fibers are tacky and they adhere together so strongly that only consolidated multifilament yarns are collected. These are drawn at room temperature 4.2×. They relax to 2.4×.

T/E/M of the consolidated yarn is 0.6 gpd/156 %/2.3 gpd. Toughness is 0.48 gpd.

As indicated hereinbefore, copending application Ser. No. 07/645,995, filed simultaneously herewith by Tietz, describes more fully various aspects of polyesters analogous to those in Example 10 herein, and details of preparation thereof.

In addition to the direct extrusion-coating of film onto a nonwoven substrate, preformed films of the polyesters of the invention have been laminated onto a nonwoven, using heat and pressure, with the film acting as its own adhesive, for instance casting 0.5, 0.75, and 1 mil films onto release paper, using similar extrusion temperatures and conditions, as described for coating, with line speed being adjusted to vary thickness. Such film on release paper may then be passed through a calendar (heated nips, one smooth and one patterned roll), with the film against the nonwoven fabric. Suitable temperatures used have been 116° C.-121° C., and 121° C.-127° C., depending on the particular materials, measured on the surface of the flat roll via thermal tapes, with a nip pressure of 10 kN, and line speed of 10 yards/minute. A variety of configurations have been used for laminating, preferably with the paper/film next to the flat roll, and the nonwoven next to the patterned roll. Higher nip pressures (up to 40 kN), with a patterned roll on either side—paper/film or nonwoven—have caused piercing/melting of the film, and unacceptable flattened and melted nonwoven aesthetics. Two flat, heated rolls may also be used, for an all-over bond, as in conventional extrusion coating.

Other means to combine film and nonwoven layers into a composite, waterproof structure include ultrasonic bonding (preferably with some discontinuous bonding pattern), and glueing (using compatible degradable hot melt adhesives), preferably, also, with a discontinuous bonding pattern, either printed into a regular pattern (as in an existing commercial backsheet), extruded in a regular pattern (e.g., series of parallel lines), or extruded in an irregular pattern (e.g., a spiral glue application system such as is commercially available, from Meltex or Nordson).

Another route is to use pressure alone to bond a nonwoven layer to a film layer (with precautions to avoid holes in the film layer of the composite), by running the layers to be bonded between the nip of 2 bonding rolls, as in a calendar, for instance, one roll being engraved with a pattern and the other flat.

Still further techniques may include using powdered degradable polymer adhesive composition to bind higher melting fibers together into a powder bonded nonwoven, to bond a degradable film to an existing degradable nonwoven; or to bond the fibers to each other and to a film, simultaneously, e.g., using a radiant or other heat source.

As will be understood by those skilled in these various arts, variations may be used to suit the materials particularly selected, such materials and commercial equipment as may be convenient and/or commercially available and/or desirable, and economic factors.

We claim:

1. A fiber and film forming polyester consisting essentially of recurring structural units of the formula

—C(O)—R—C(O)—OGO— wherein R is
about 97 to 99.9 mole % para-phenylene and
about 0.1 to 2.5 mole % of the sulfonate radical,

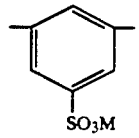

where M is
an alkali metal or alkaline earth metal,
and wherein G is
at least about 13% by weight of a radical of a polyalkylene glycol of molecular weight at least about 250, and
up to about 40 mole % of a polyethylene ether radical selected from the group consisting of —(CH$_2$)$_2$—O—(CH$_2$)$_2$— and —(CH$_2$)$_2$—O—(CH$_2$)$_2$—O—(CH$_2$)$_2$—,
with the remainder being selected from the group consisting of —(CH$_2$)$_2$—, —(CH$_2$)$_3$— and —(CH$_2$)$_4$—.

2. Polyester according to claim 1, wherein R is about 98 to 98.5 mole % para-phenylene and about 1.5 to 2% of the sulfonate radical, and G contains about 15% to 20% by weight of the polyalkylene glycol radical.

3. A fiber of the polyester of claim 1.
4. A fiber of the polyester of claim 2.
5. A non-woven sheet of the polyester of claim 1.
6. A non-woven sheet of the polyester of claim 2.
7. A film of the polyester of claim 1 or 2.
8. A composite film of the polyester of claim 1 or 2 and of a layer of nonwoven sheet.
9. A disposable diaper which includes an absorbent body portion having on one surface thereof a water permeable nonwoven sheet of fibers of the polyester of claim 1 or 2.
10. A disposable diaper which includes an absorbent body portion having on one surface thereof a water impermeable film of the polyester of claim 1 or 2.
11. A fiber and film forming copolyester consisting essentially of about 60%-98% by weight of the copolyester being recurring structural units (1) of the formula

—C(O)—R—C(O)—OGO— wherein R is
about 93 to 99.9 mole % para-phenylene
and about 0.1 to 2.5 mole % of the sulfonate radical

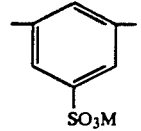

where M is
an alkali metal or alkaline earth metal,
and wherein G is
at least about 13% by weight of a radical of a polyalkylene glycol of molecular weight at least about 250, and
up to about 40 mole % of a polyethylene ether radical selected from the group consisting of —(CH$_2$)$_2$—O—(CH$_2$)$_2$— and —(CH$_2$)$_2$—O—(CH$_2$)$_2$—O—(CH$_2$)$_2$—,
with the remainder being selected from the group consisting of —(CH$_2$)$_2$—, —(CH$_2$)$_3$— and —(CH$_2$)$_4$—, and about 2% to 40% by weight of the copolyester being structural units (2) of the formula [—C(O)—Q—O—]$_n$, and Q are such that the hydroxy acid HO-13 C(O)—Q—OH and/or the polyhydroxyacid HO[—C(O)—Q—O—]$_n$H has a melting point at least 5° C. lower than its composition temperature.

12. A copolyester according to claim 11, wherein Q is selected from the group consisting of —CH$_2$—, —CH$_2$—CH$_2$—, —CH$_2$—CH$_2$—CH$_2$—, —C(R')H—, —(CH$_2$)$_5$—, and —C(R')H—CH$_2$—, where R' is selected from the group consisting of —CH$_3$ and —CH$_2$—CH$_3$.

* * * * *